(12) United States Patent
Pool

(10) Patent No.: US 6,806,092 B1
(45) Date of Patent: Oct. 19, 2004

(54) COMBUSTION GAS DETECTION SYSTEM

(75) Inventor: James L. Pool, Clarinda, IA (US)

(73) Assignee: The Lisle Corporation, Clarinda, IA (US)

( * ) Notice: Subject to any disclaimer, the term of this patent is extended or adjusted under 35 U.S.C. 154(b) by 402 days.

(21) Appl. No.: 09/932,864

(22) Filed: Aug. 17, 2001

(51) Int. Cl.[7] .......................... G01N 33/22; G01N 21/75
(52) U.S. Cl. ........................ 436/137; 436/164; 436/167; 436/168
(58) Field of Search ................................ 436/137, 164, 436/167, 168; 422/55, 58, 83, 86, 88; 60/272, 276–279, 282, 288

(56) References Cited

U.S. PATENT DOCUMENTS 4,098,577 A * 7/1978 Halpern .......................... 436/1

FOREIGN PATENT DOCUMENTS

| BE | 1003418 A | * | 3/1992 | ............ F02B/00/00 |
| EP | 122975 A1 | * | 10/1984 | ............ F01P/11/14 |
| GB | 1438913 A | * | 6/1976 | ............ G01N/21/06 |
| ZA | 8500226 A | * | 7/1985 | ............ F02B/00/00 |

OTHER PUBLICATIONS

Cal–Van Tools Catalog, p. 21, Model No. 560, "Leak–Check".

* cited by examiner

*Primary Examiner*—Yelena Gakh
(74) *Attorney, Agent, or Firm*—Banner & Witcoff, Ltd.

(57) ABSTRACT

A combustion gas detection apparatus includes a transparent tube partially filled with a combustion gas sensing fluid and an inlet fitting for engagement with the radiator cap of an engine cooling system and an outlet fitting connected with a vacuum port of the engine.

5 Claims, 1 Drawing Sheet

COMBUSTION GAS DETECTION SYSTEM

BACKGROUND OF THE INVENTION

In a principal aspect the present invention relates to a combustion gas detection system for use in detecting undesired combustion gases in the coolant of the cooling system for an internal combustion engine.

When servicing an internal combustion engine of a motor vehicle, a mechanic or vehicle service technician often finds that it is appropriate or desirable to investigate whether the exhaust system is leaking combustion gases into the coolant of the cooling system. For example, a crack in the vehicle engine block may result in the transmission of combustion gases into the coolant liquid of the engine cooling system. Obviously, such a condition is very undesirable and indicates a necessity for potential repair or replacement of the engine block, engine head, or other potential sources of combustion gas leakage into the cooling system.

Heretofore, a method and apparatus for detection of such combustion gases involved suction of gases from the radiator outlet of an engine cooling system by squeezing a bulb to withdraw the gases through a container of gas sensitive fluid. The mechanic or technician would rapidly pump on the rubber bulb in order to withdraw the gases through the fluid. The fluid, being sensitive to the combustion gases, would reveal the presence of combustion gases by a change of color, for example.

While such a system has proven to be useful in detecting gases, there has remained a need for an improved apparatus and method for investigating the presence of combustion gases in the coolant fluid of a cooling system for an internal combustion engine.

SUMMARY OF THE INVENTION

Briefly, the present invention comprises a combustion gas detection system which includes a transparent or translucent tube filled with combustion gas sensitive fluid. The tube includes an inlet fitting at one end which is adapted to engage and seal with the radiator cap opening of a vehicle cooling system. A check valve in a passage through the fitting leading from the radiator cap opening into the tube prevents backflow of fluid from the tube and permits inflow of gas from the cooling system. An outlet fitting for the fluid containing tube includes a flexible suction hose or conduit adapted to engage with a vacuum port of the vehicle engine. By engaging the engine vacuum port, the flexible conduit enables suction of fluid or gas from the cooling system through the transparent tube and the fluid in the tube.

When testing for combustion gas utilizing the device of the invention, the technician will start the internal combustion engine and permit it to warm to normal operating temperature. Some of the coolant fluid is removed from the cooling system so that there is a region of gas above the fluid level within the radiator. The inlet fitting of the fluid filled transparent tube is then engaged over the radiator cap opening, and an engine vacuum port leading from the tube is engaged or connected with the suction hose from the transparent tube to thereby draw gas from the cooling system through the transparent tube. The gas sensitive fluid within the detection device transparent tube typically will change color as combustion or exhaust gases react therewith to alter the pH of the fluid. By way of example, the fluid within the detection device transparent tube may be a mixture of bromothymol blue, sodium monocarbonate and water. The presence of excess carbon dioxide and/or carbon monoxide will cause such a solution to alter color from a blue color to a yellow hue.

When attempting to troubleshoot the operation of an internal combustion engine by locating the cylinder or cylinders wherein the source of combustion gas leakage occurs, removal of the ignition spark associated with each cylinder may be effected. By removing the ignition mechanism associated with one or more cylinders, a mechanic will remove that cylinder or cylinders as an exhaust gas source and by process of elimination will be able to identify whether a particular cylinder is the source of the undesired combustion gas.

Thus, it is an object of the invention to provide an improved combustion gas detection apparatus or system and method for use with internal combustion engines.

A further object of the invention is to provide a combustion gas detection apparatus which is easy to use, foolproof, rugged and economical.

These and other objects, advantages and features of the invention will be set forth in a detailed description which follows.

BRIEF DESCRIPTION OF THE DRAWING

In the detailed description which follows, reference will be made to the drawing comprised of the following figures.

DESCRIPTION OF THE PREFERRED EMBODIMENT

Figure 1:
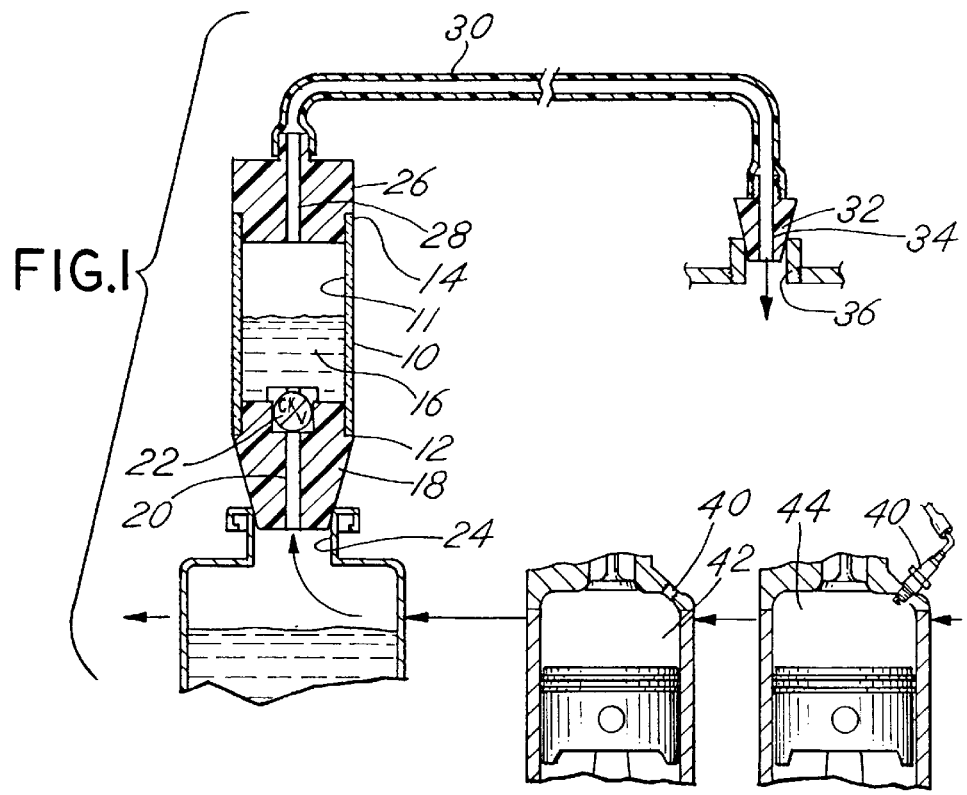
FIG. 1 is a plan view of the apparatus of the invention depicted in combination with various components of an internal combustion engine.
Figure 2:
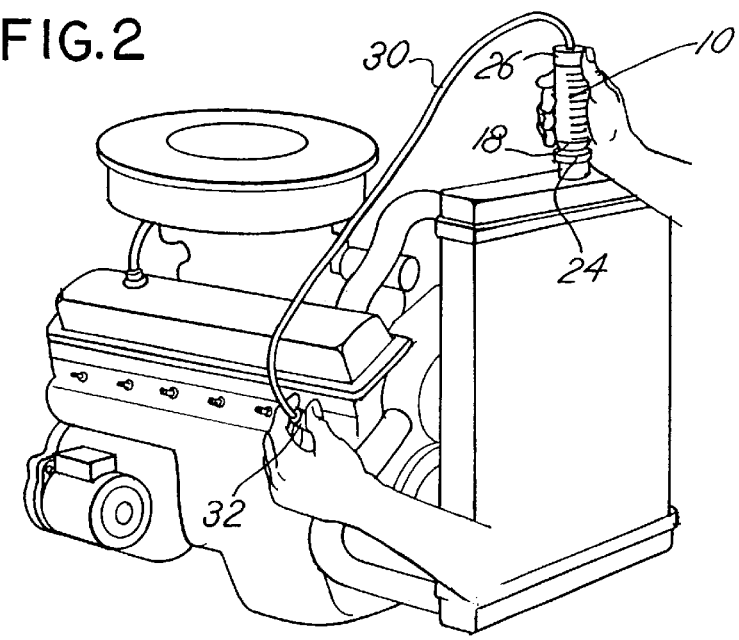
FIG. 2 is an isometric view of the apparatus of the invention as it is used in combination with an internal combustion engine for detection of combustion gas.

Referring to the figures, the apparatus includes a main cylindrical tube 10 having an inlet end 12 and an outlet end 14. Preferably, the tube 10 is translucent or transparent. Most preferably, the tube is transparent in order that one might easily observe the color change of fluid 16 within the tube 10. Various indicia may be provided in the side of the tube 10 to indicate the level of fluid therein.

An inlet fitting 18 is provided at the inlet end 12 of the tube 10. The inlet fitting 18 includes a throughpassage 20 with a check valve 22 therein. The check valve 22 permits movement of gas into the tube 10 and prevents backflow of liquid, gas sensitive fluid from the tube 10 through the passageway, or throughpassage 20. Typically, the fitting 18 is made from an elastomeric material in order that it might tightly seal against an opening associated with a cooling system, for example, a radiator opening 24.

An outlet fitting 26 is provided at the outlet end 14 of the tube 10. The outlet fitting 26 includes a throughpassage 28 leading from the interior or reservoir 11 of the tube 10. A flexible conduit or hose, for example, rubber or Tygon plastic tubing 30 is fitted into the outlet fitting 26 and is connected with the passage 28. The opposite end of the tubing or conduit 30 includes a vacuum port connector or fitting 32 with a passage 34 therethrough. The vacuum port fitting 32 is preferably an elastomeric fitting so that it may be sealed in a vacuum port of an internal combustion engine, for example, vacuum port 36.

A combustion gas sensitive fluid 16 is retained within the reservoir 11 of the tube 10. For example, the fluid 16 may be the following mix: bromothymol blue, sodium monocarbonate and water. However, other combustion gas sensitive fluids may be used. The particular combustion gas sensitive material identified will change color from blue to yellow upon sensing of combustion gases, that is carbon dioxide and/or carbon monoxide.

In operation, after removal of some of the cooling fluid from the vehicle radiator, the inlet fitting 18 is sealed against the open radiator cap fitting 24 prior to or subsequent to starting of the vehicle engine. The engine is then run so that it is operating at its normal operating temperature. This permits access to any gases that may be in the coolant cycling through the cooling system. The vacuum port fitting 32 is then placed into a vacuum port 36 of the engine. There are many such vacuum ports on internal combustion engines and any one of them can be used for this purpose. Connecting the vacuum port fitting 32 to the vacuum port 36 will effect a flow of gas through the passage 20, check valve 22, fluid 16 and then through the passage 28 and conduit 30. As the gas flows through the detection fluid 16, it will react therewith, assuming it is combustion gas, as evidenced by a color change in the fluid 16. The gas that is leaking into the coolant would, in all likelihood, be from the engine block or some other similar source.

The combustion gas source may be detected by disengaging the ignition system with one or more of the engine cylinders. For example, an ignition system 40 associated with a cylinder 42 may be disconnected. Thus, if combustion gas is detected when that cylinder is not firing, the combustion gas would be associated with another active cylinder 44 rather than the inactive cylinder 42. In this manner, a technician or mechanic may troubleshoot and determine the source of the combustion gas.

It is possible to vary the construction of the apparatus. The shape and size of the tube 10 may be varied. A series of tubes 10 may be provided filled with different fluids and separated by check valves to detect different levels and contaminants of gas. The shape and size of the various fittings may be altered. Connection of the vacuum port fitting to the internal combustion engine being checked may also be varied. That is, a separate vacuum port source may be utilized. Thus, the invention is to be limited only by the following claims and equivalents thereof.

What is claimed is:

1. A method for detection of combustion gases in the coolant system of an internal combustion engine of the type having an access opening to the cooling system and an engine vacuum port, said method comprising the steps of:

providing a detection apparatus having a transparent tube filled inside, at least in part, with combustion gas sensitive fluid; said tube including an inlet fitting with a throughpassage to the tube, the throughpassage including a check valve to block fluid flow from the tube, and a vacuum conduit with an engine vacuum port connection member from the tube;

operating the engine with an open cooling system access opening;

connecting the vacuum conduit vacuum port connection member to an engine vacuum port of said engine, connecting the inlet fitting to the cooling system access opening of said engine to thereby draw a gas flow from the cooling system through the fluid; and observing the fluid to detect any visual change indicative of combustion gas derived from the cooling system.

2. The method of claim 1 wherein the fluid is a mixture of bromothymol blue, sodium monocarbonate and water.

3. The method of claim 1 wherein the fluid is sensitive to gases selected from the group consisting of carbon dioxide, carbon monoxide, and mixtures thereof.

4. The method of claim 1 including the step of disconnecting one or more engine cylinders from its combustion cycle whereby the disconnected cylinder will be eliminated or identified as a combustion gas source.

5. The method of claim 1 wherein the vacuum port connection member is elastomeric.

\* \* \* \* \*